(12) United States Patent
Lyngstadaas et al.

(10) Patent No.: US 7,033,611 B2
(45) Date of Patent: Apr. 25, 2006

(54) MATRIX PROTEIN COMPOSITIONS FOR GUIDED CONNECTIVE TISSUE GROWTH

(75) Inventors: Ståle Petter Lyngstadaas, Nesoddtangen (NO); Stina Gestrelius, Lund (SE)

(73) Assignee: Biora Bioex AB, Malmo (SE)

( * ) Notice: Subject to any disclaimer, the term of this patent is extended or adjusted under 35 U.S.C. 154(b) by 0 days.

(21) Appl. No.: 10/468,939

(22) PCT Filed: Feb. 21, 2002

(86) PCT No.: PCT/IB02/02110

§ 371 (c)(1),
(2), (4) Date: Aug. 22, 2003

(87) PCT Pub. No.: WO02/080994

PCT Pub. Date: Oct. 17, 2002

(65) Prior Publication Data

US 2004/0072727 A1    Apr. 15, 2004

(30) Foreign Application Priority Data

Feb. 23, 2001 (DK) ................... PA 2001 00311

(51) Int. Cl.
*A61K 35/32* (2006.01)
*A61K 38/39* (2006.01)

(52) U.S. Cl. ........................... 424/549; 514/2

(58) Field of Classification Search ............ 514/2
See application file for complete search history.

(56) References Cited

U.S. PATENT DOCUMENTS 5,605,930 A * 2/1997 Samid ................ 514/510
6,503,539 B1 * 1/2003 Gestrelius et al. ......... 424/549

FOREIGN PATENT DOCUMENTS

WO    WO 99/43344    9/1999
WO    WO 00/53197    9/2000

OTHER PUBLICATIONS

Database Medline, "In Vitro Wound Healing Responses to Enamel Matrix Derivative", Database Accession No. 2001066181 XP002169286 (2000).

* cited by examiner

Primary Examiner—Jon Weber
Assistant Examiner—Anand U. Desai
(74) Attorney, Agent, or Firm—Kudirka & Jobse, LLP

(57) ABSTRACT

The present invention relates to the use of enamel matrix, enamel matrix derivatives and/or enamel matrix proteins as therapeutic and/or cosmetic agents. These substances are used for the manufacture of a pharmaceutical and/or cosmetic composition for actively inducing, guiding and/or stimulating connective tissue growth and thus to prevent connective tissue scarring and/or contraction in a wound cavity and/or tissue defect that is characterized by a substantial loss of tissue. The invention comprises, in particular, the use of active enamel substances for guided connective soft tissue growth and resistance to contraction in deep cavity shaped wounds following loss or removal of significant volumes of tissue, such as e.g., after surgical removal of a tumor and especially in combination with radiation therapy.

44 Claims, 6 Drawing Sheets

MATRIX PROTEIN COMPOSITIONS FOR GUIDED CONNECTIVE TISSUE GROWTH

FIELD OF THE INVENTION

Figure 1:
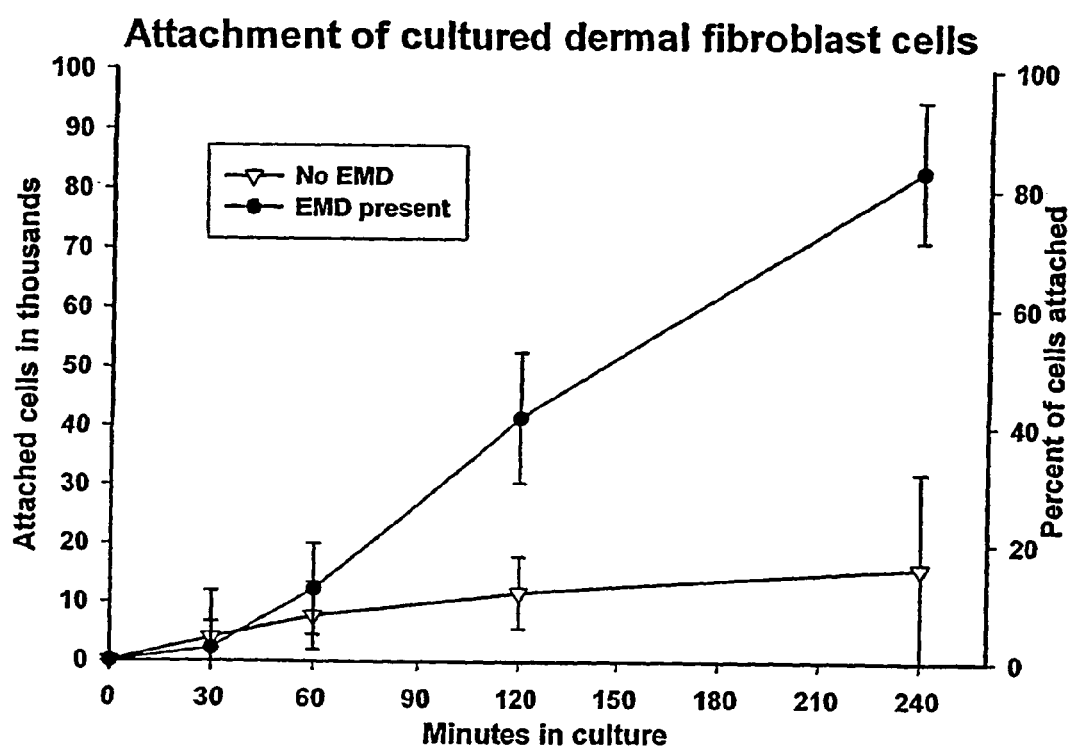

The present invention relates to the use of enamel matrix, enamel matrix derivatives and/or enamel matrix proteins as therapeutic, as prophylactic and/or as cosmetic agents. In the present invention, said substances are shown to actively induce, guide and/or stimulate connective tissue growth and to be involved in preventing connective tissue scaring and/or contraction. Comprised in the invention is in particular the use of active enamel substances for guided connective soft tissue growth and resistance to contraction in deep cavity shaped wounds following loss or removal of significant volumes of tissue, such as e.g. after surgical removal of a tumour and especially in combination with radiation therapy.

BACKGROUND OF THE INVENTION

Removal of a significant volume of tissue, as is frequently necessary in cancer surgery, confronts the surgeon with special technical and physiological problems. Removal of a significant volume of tissue often makes it difficult to close the wound properly, and when closing is achieved, the tissue scars and the stitches restrict the mobility, which disabilitates the patient. The enclosed wounds can collapse or fill with fluids and cell poor scar tissues. The results are often disabling scar tissue formation, infections, pain, cosmetic anomalies or even complete loss of function of the effected body parts. For example, after surgical removal of a breast tumour, the contraction of the wound cavity often leads to shrinkage of the breast that by far exceeds the volume of the originally removed tissue. Furthermore, adjuvant radiation therapy increases the above mentioned problems drastically. Today, these post-surgical conditions are treated by silicon inlays, secondary palliative surgery, pain and infection controlling drugs, or in the worst case by amputation. Needles to say, these conditions and measurements all cause severe problems for the patients, physically, esthetical and emotionally.

Enamel matrix proteins, present in the enamel matrix, are most well-known as precursors to enamel. Prior to cementum formation, enamel matrix proteins are deposited on the root surface at the apical end of the developing tooth-root. There is evidence that the deposited enamel matrix is the initiating factor for the formation of cementum. Again, the formation of cementum in itself is associated with the development of the periodontal ligament and the alveolar bone. As shown by the present inventors prior to the present invention, enamel matrix proteins can therefore promote periodontal regeneration through mimicking the natural attachment development in the tooth (Gestrelius S, Lyngstadaas SP, Hammarström L. Emdogain—periodontal regeneration based on biomimicry. Clin Oral Invest 4:120–125 (2000).

The enamel matrix is composed of a number of proteins, such as amelogenin, enamelin, tuft protein, proteases, and albumin. Amelogenins, the major constituent of the enamel matrix, are a family of hydrophobic proteins derived from a single gene by alternative splicing and controlled post secretory processing. They are highly conserved throughout vertebrate evolution and demonstrate a high overall level of sequence homology among all higher vertebrates examined (>80%). In fact, the sequences of porcine and human amelogenin gene transcript differ only in 4% of the bases. Thus, enamel matrix proteins, although of porcine origin, are considered "self" when encountered in the human body and can promote dental regeneration in humans without triggering allergic responses or other undesirable reactions.

Enamel matrix derivative (EMD), in the form of a purified acid extract of proteins from pig enamel matrix has previously been successfully employed to restore functional periodontal ligament, cementum and alveolar bone in patients with severe tooth attachment loss (Hammarström et al., 1997, Journal of Clinical Periodontology 24, 658–668).

In studies on cultured periodontal ligament cells (PDL), it was furthermore shown that the attachment rate, growth and metabolism of these cells were significantly increased when EMD was present in the cultures. Also, cells exposed to EMD showed increased intracellular cAMP signalling and autocrine production of growth factors, when compared to controls. Epithelial cells on the other hand, increased cAMP signalling and growth factor secretion when EMD was present, but their proliferation and growth were inhibited (Lyngstadaas et al., 2001, Journal of Clinical Periodontology 28, 181–188).

Enamel proteins and enamel matrix derivatives have previously been described in the patent literature to be able to induce hard tissue formation (i.e. enamel formation, U.S. Pat. No. 4,672,032 (Slavkin)), binding between hard tissues (EP-B-0 337 967 and EP-B0 263 086) and open wound healing, such as of skin and mucosa (WO 9943344).

The present application relates to the beneficial effects of EMD on guided connective soft tissue growth and resistance to contraction in closed wounds following loss or removal of significant volumes of tissue, such as e.g. after tumour surgery and especially in combination with radiation therapy, effects that are both unexpected and surprising.

DISCLOSURE OF THE INVENTION

Maintenance, repair and regeneration of differentiated tissue is guided by several tissue specific growth factors. However, so far all attempts to apply individual growth factors to regeneration of human tissue in therapy have failed in clinical trials. This is thought to be due to growth factors being pluripotent signal factors that work in concert. In an intricate teamwork, they induce and modulate tissue growth, differentiation and maturation during development and orchestrate healing, repair and regeneration of diseased tissue. The enamel matrix derivatives (EMD) of the present invention, however, are able to circumvent this problem, as they can induce not only one but an orchestrated cascade of factors naturally found in tissues developing adjacent to the enamel matrix. They mimic the natural environment of a developing tissue and thus mimic a natural stimulation for tissue regeneration, cell differentiation and/or maturation.

The present invention is based on the surprising finding that enamel matrix, enamel matrix derivatives and/or enamel matrix proteins (the term "an active enamel substance" is in the following also used for an enamel matrix, an enamel matrix derivative or an enamel matrix protein) do not only promote periodontal ligament cell growth, but also stimulate non-periodontal fibroblast cell growth and differentiation, whereas epithelial cell growth or differentiation is not stimulated by the presence of active enamel substances. The use of a pharmaceutical or cosmetical composition comprising an active enamel substance, as described in the present invention, thus relates to the selective stimulation of mesodermal and/or endodermal cell growth, including growth of cartilage, bone and connective tissue, striated and smooth muscles, the heart, blood and lymph vessels and cells, the kidneys, gonades (ovaries and testes), the genital ducts, serous membranes lining the body cavities (pericardial, pleural and peritoneal), the spleen, the cortex of the suprarenal gland, the epithelial lining of the gastrointestinal and respiratory tracts, the parenchyma of the tonsils, thyroid gland, parathyroid glands, thymus, liver and pancreas, the epithelial lining of the urinary bladder and most of the ureta, the epithelial lining of the tympanic cavity, tympanic antrum and auditory tube, as opposed to ectodermal cell growth including growth of the central or peripheral nervous system, the epidermis and its appendages (hair and nails), the mammary glands, pituitary gland, the subcutaneous glands and the enamel of teeth, which is not stimulated by the application of said composition comprising an active enamel substance.

As shown by the present inventors (see experiment 1), the increased attachment rate of non-periodontal fibroblast cells that grow on active enamel substances demonstrates that an enamel protein based matrix mimics an extracellular matrix. This mimicry facilitates rapid attachment of these cells. The observed rise in growth rate and metabolism in these fibroblast cells, growing on active enamel substances, further proves that active enamel substances provide an extracellular matrix that stimulates fibroblast cells to speed up their metabolism. Also, a rise in growth rate is reflected in the increase of DNA synthesis, indicating that cell proliferation is up-regulated in these cultures. Furthermore, since the increase in utilisation of [$^{35}$S]-methionine in these fibroblast cells exceeds the rise in growth rate, some of the added metabolic activity also reflects a boosted anabolism and/or secretion of extracellular proteins.

The surprising findings described above lead to the envisioning of substantially new possibilities for the use of active enamel substances. One embodiment, described in the present invention, comprises the use of active enamel substances for preparing a pharmaceutical or cosmetical composition that is to be used as a fill-in application for significant tissue loss wounds that would otherwise lead to painful and/or disfiguring scarring of a mammal's body. The successful application of said composition, as described herein, leads to increased neogenesis and tissue-specific gain of soft tissue, muscle, blood and lymph vessels, tendons, and cartilage.

Not intended to be within the scope of the present invention is the treatment of shallow open wounds in soft tissue with active enamel substances.

A preferred embodiment of the present invention relates to the use of an active enamel substance for the preparation of a pharmaceutical or cosmetic composition that is used as a beneficial agent for the enhancement or improvement of guided connective tissue growth into soft tissue defects following significant tissue loss due to trauma, infectious diseases, necrosis, removal of neoplasms or other cytoreductive surgical interventions. As demonstrated in the experimental section herein, the active enamel substance exerts especially useful effects in guiding and stimulating connective tissue growth into a significant tissue loss following the surgical removal of a tumour. Further, another preferred embodiment relates to the use of said active enamel substance for the preparation of a pharmaceutical or cosmetic composition for guiding and stimulating connective tissue growth following post surgical tumour treatment after significant tissue loss, such as after radiation therapy.

The present invention thus provides optimal means to refill a loss of tissue that is left from a surgically removed tissue, such as e.g. a tumour, with new fibroblasts that are stimulated to proliferate in the wound cavity. To this means, the cavity is filled with a preparation of active enamel substances, such as e.g. with EMDOGAIN® (BIORA AB, Sweden), which will successively be degraded and replaced by new fibroblasts. Thereby, the cavity will be protected from collapsing and the surrounding tissue will be protected from contracting, and finally, the new grown soft tissue will act as a natural replacement for the surgically removed tissue. Furthermore, the unique property of active enamel substances to stimulate proliferation and differentiation of selective tissue types, will in the above mentioned embodiment only stimulate the neogenesis of mesodermal or endodermal cells, but not stimulate any ectodermal cell growth.

In an especially preferred embodiment of the invention, an active enamel substances can therefore be used for the preparation of a pharmaceutical or cosmetic composition for filling of a cavity wound that is characterised by substantial loss of tissue after surgical removal of a breast tumour. Breast tumours are mainly glandular tumours, i.e. that active enamel substances will not stimulate the regrowth of the tumour tissue, glands being of ectodermal origin, but only stimulate the fill-in of the cavity with new connective tissue. In a later scenario, a person skilled in the art will have no difficulties to further envision the stimulation of regrowth of blood vessels and innervation that will follow the fibrotic fill-in of the wound.

The use of a composition comprising an active enamel substance, as described in the present invention, will prevent contraction of connective tissue, following significant tissue loss due to surgical tumour treatment such as surgical removal of significant tumour tissue and post surgical tumour treatment, such as, for example but not exclusively, radiation therapy. The use of active enamel substances in accordance to this invention in a tension-free closure may be associated with less pain and less incidence of postoperative fluid accumulation (seroma). Furthermore, compositions comprising an active enamel substance will also help increase tensile strength of the wound and thus be beneficial for improving yet another aspect of the repair process.

Accordingly, the invention relates to the use of an active enamel substance for the preparation of a pharmaceutical or cosmetic composition i) for improving connective tissue fill of a significant tissue loss and/or defect, and/or ii) for avoiding soft tissue contraction following significant tissue loss due to e.g. tumour removal and thus limiting post surgical therapy complications.

LEGENDS TO FIGURES

FIG. 1: Normal Human Dermal Fibroblast (NHDF) cell attachment rate during the first hours after seeding is nearly five times more efficient when the surface of the culture dish is coated with EMD. n=6 error bars give ±SD FIG. 2: Density plot of cultured NHDF cells show that cells growing in presence of EMD proliferate faster than controls. Five different areas in each culture were counted in each of six parallel cultures at each time point (n=30), error bars are ±SD.

Figure 3:
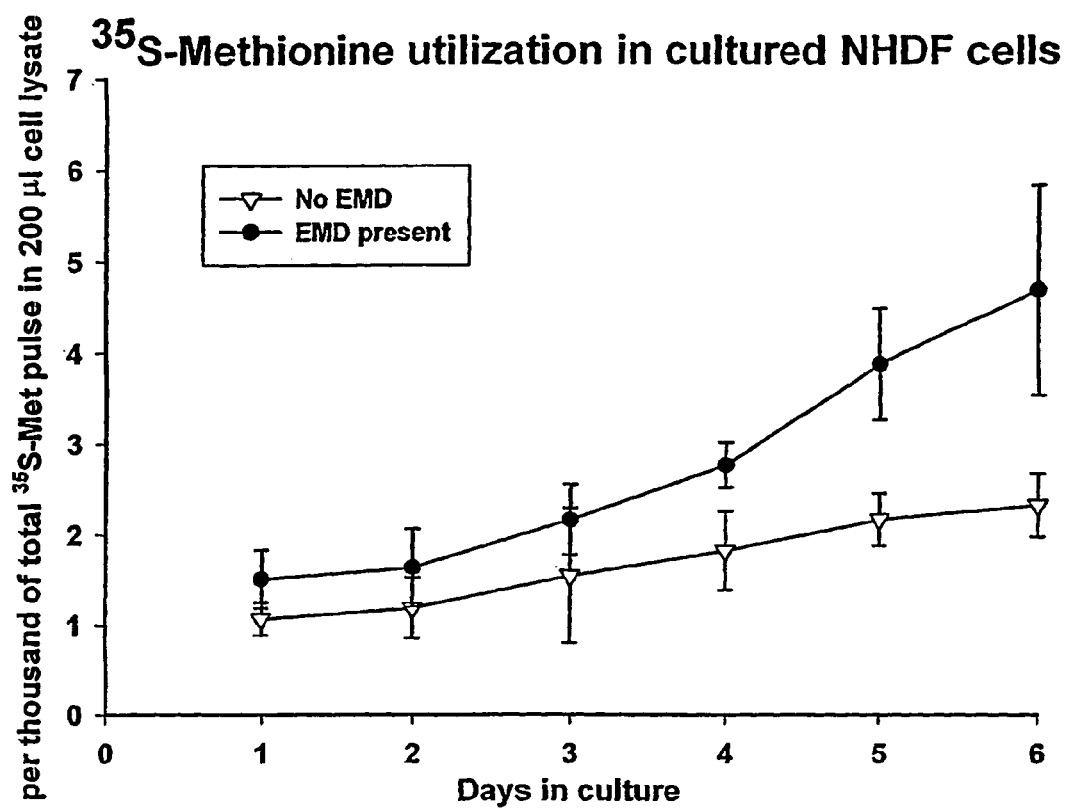

FIG. 3: Utilization of [$^{35}$S]methionine pulse plotted against days in NHDF cultures after seeding. The presence of EMD in the cultures significantly increases the metabolic rate of NHDF cells. n=9, error bars give ±SD.

Figure 4:
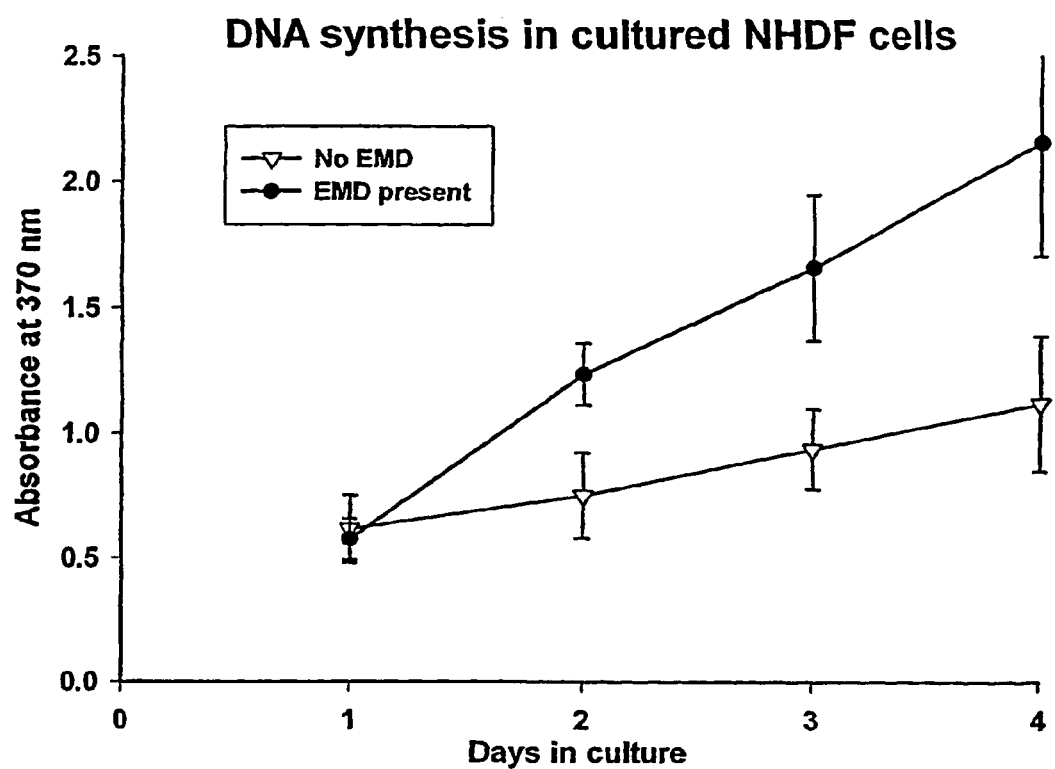

FIG. 4: DNA synthesis analyzed by BrdU incorporation during DNA replication show that NHDF cells significantly increase synthesis of nucleic acids in presence of EMD. n=6, error bars give ±SD.

Figure 5A:
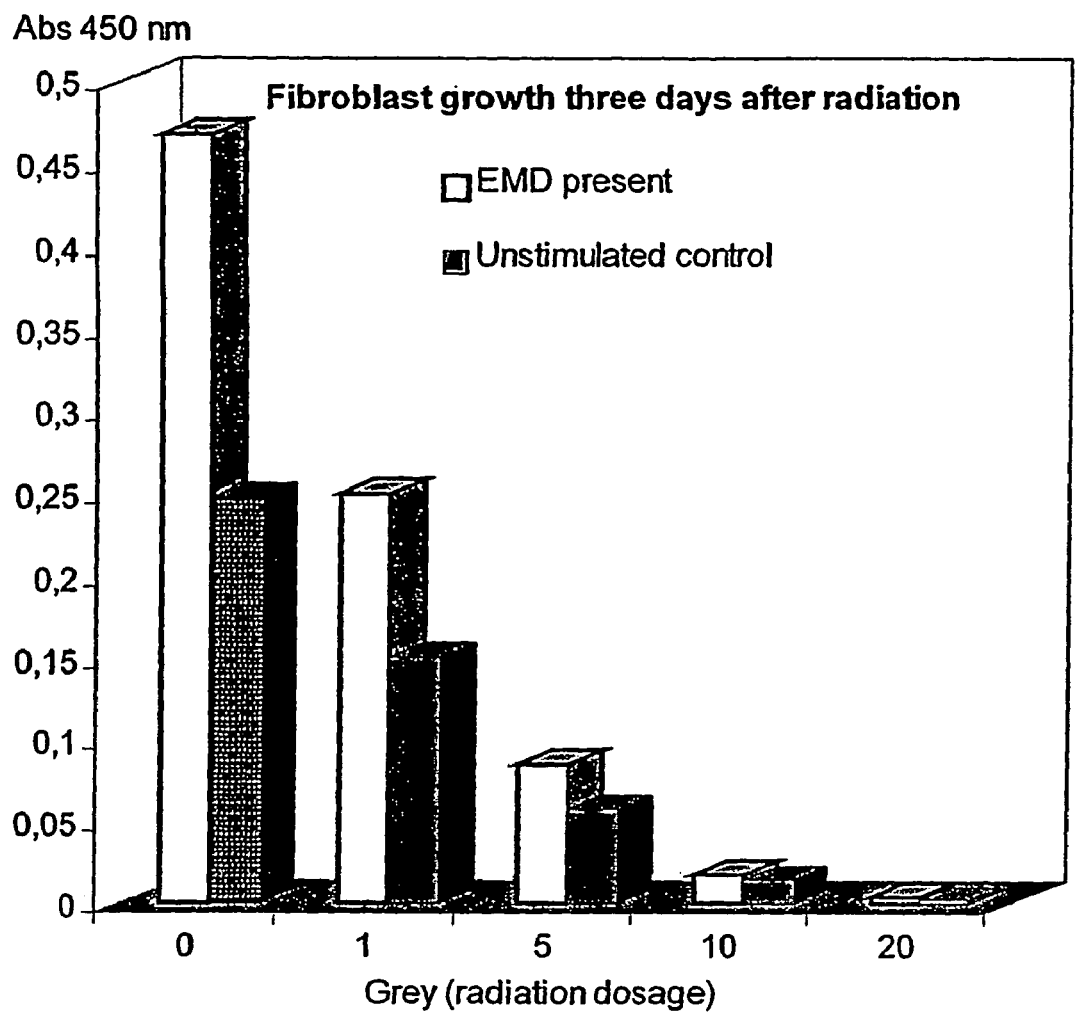
Figure 5B:
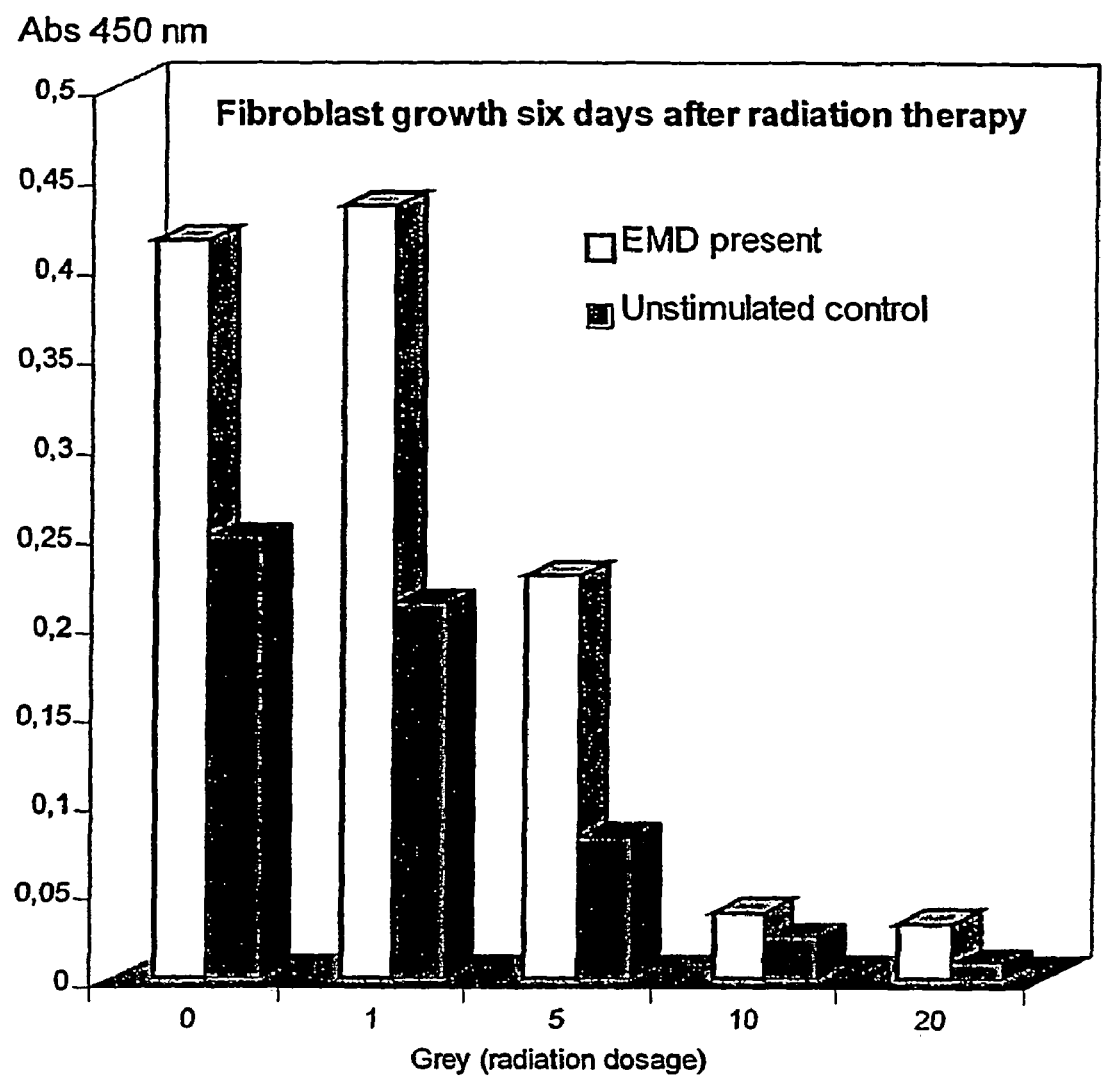

FIG. 5: Radiated cells growing in the presence of EMD increase their number twice as fast as unstimulated cultures (FIGS. 5A and 5B)

DETAILED DISCLOSURE

The present invention relates to the use of enamel matrix, enamel matrix derivatives and/or enamel matrix proteins for actively inducing, guiding and/or stimulating connective tissue growth and for being involved in preventing connective tissue scaring and/or contraction in deep cavity wound healing.

The majority of tissue cavities and defects are filled through reparative processes, i.e. the new tissue that is formed (scar tissue) is often of different volume and structurally and chemically unlike the original tissue. In the early stage of the tissue repair, one process is almost always involved, the formation of a transient connective tissue in the area of the tissue injury. This process starts by forming of a new extracellular collagen matrix by fibroblasts. Said new extracellular collagen matrix supports the connective tissue during the final healing process. However, in defects wherein a significant volume of tissue has been removed or lost, the defect or deep tissue-cavity will not fill with connective tissue and extracellular collagen based matrix, but a significant part of the defect volume will fill with cell free exudate from the surrounding tissue. To allow for connective tissue fill of the whole cavity, the exudate has to be drained out so that matrix formation and subsequent connective tissue growth can occupy most of the cavity.

Under normal circumstances, the body provides mechanisms for healing tissue cavities in order to restore the function and integrity of the involved tissue or body part. However, the recovering time can be very long and the defect may persist for an extended period of time, i.e. months or even years. During this time, the patient is often disabled and suffers from pain, discomfort and complications that need regular professional attendance.

The repair of tissue defects and/or cavities follows the classical wound healing stages that normally include inflammation (normally 1–3 days), migration (normally 1–6 days), proliferation (normally 3–24 days) and maturation (normally 1–12 months). The healing process is a complex and well-orchestrated physiological process that involves migration, proliferation and differentiation of a variety of cell types as well as synthesis of matrix components.

The healing process may be separated into the following three phases:

i) Haemostasis and Inflammation

When platelets are present outside the circulatory system and exposed to thrombin and collagen, they become activated and they aggregate. Thus, platelets initiate the repair process by aggregating and forming a temporary plug to ensure haemostasis and prevent invasion from bacteria. The activated platelets initiate the coagulation system and release growth factors like platelet-derived growth factor (PDGF) and epidermal growth factors (EGFs) and transforming growth factors (TGFs).

The first cells to invade the wound area are neutrophils followed by monocytes which are activated by macrophages.

The major role of neutrophils appears to be clearing the wound of contaminating bacteria or defending the wound against contaminating bacteria and to improve the healing of the wound by removing dead cells and platelets. The infiltration of neutrophils ceases within about the first 48 hours, provided that no bacterial contamination is present in the wound. Excess neutrophils are phagocytosed by tissue macrophages recruited from the circulating pool of blood-borne monocytes. Macrophages are believed to be essential for efficient wound healing in that they are also responsible for phagocytosis of pathogenic organisms and a clearing up of tissue debris. Furthermore, they release numerous factors involved in subsequent events of the healing process. The macrophages attract fibroblasts that start the production of collagen.

ii) Granulation Tissue Formation

Within 48 hours after wounding, fibroblasts begin to proliferate and migrate into the wound space from the connective tissue at the wound edge. The fibroblasts produce collagens and glycosaminoglycans and inter alia low oxygen tension at the wound stimulates proliferation of endothelial cells. The endothelial cells give rise to the formation of a new capillary network. At this stage, the wound area, i.e. the cavity, is further decreased by contraction. In the case of deep, cavity-like, soft tissue enclosed defects, e.g. like those present following surgical removal of a breast tumour, this contraction affects both the appearance of the body part as well as the performance, and often causes pain and discomfort.

At this stage, if necessary as adjuvant therapy after removal of malignant tumours, radiation therapy is applied. Said therapy aims at removing residual cancer cells and local metastases from the tissue or body part that has been treated. Besides killing all proliferating cancer cells, this therapy also affects all normal cells that are undergoing mitosis, and imposes structural damage to DNA and proteins in the repairing tissue. The effect of this damage is a severe slow down of the cellular repair processes, while the extracellular processes remain mostly unaffected. With time, this induced imbalance between cellular growth and extracellular processes causes severe contractions of the wound surfaces and thus the cavity and/or defect. These contractions are often so painful and disfiguring that the tissue or body part in question is removed and substituted by prosthesis where possible, e.g. removal of major part of the breast and reconstruction by silicon inlay. In the cases where removal is not compatible with life, reconstructive surgery is the only option. However, because of the radiation damage to the DNA, the tissue does not have the ability to conduct the normal repair sequence and the chances are that the new surgical defect also undergoes contraction with subsequent need for even more reconstructive surgery.

iii) Tissue Remodelling

As soon as the defect is completely filled with scar tissue, remodelling of the tissue begins. During this phase the scar tissue is substituted with a more organised type of tissue that aims at restoring the strength, function, performance and appearance of the tissue/body part in question. This phase typically lasts for several years after the initial defect. Also this stage is severely hampered by radiation therapy that causes contraction and scarring.

All of the above-mentioned processes take considerable time. The rate of healing is influenced by the wound's freedom from infection, the general health of the individual, presence of foreign bodies, etc. Some pathologic conditions like infection, maceration, drying out, generally poor health and malnutrition can, if left untreated for a longer time, lead to formation of a chronically inflamed or infected tissue defect or cavity that is very difficult to cure. Furthermore, since the primary defect is caused by removal of significant volumes of tissue, surgical removal of the defunct tissue is not desirable or even possible. These conditions therefore severely affect the quality of life of a patient and can also be extremely disabling or even life threatening.

Traditionally, cavity like, soft tissue defects have been treated by closing them with sutures with a draining device present that allows wound exudate and puss to escape from the cavity during the initial phases of the healing process. While favourable for cellular filling of the defect, this strategy delays the healing because a foreign body is left in the wound that can provoke inflammation and makes a gateway for invading micro flora. Delayed wound healing or inflammation can exacerbate fibrosis and subsequent tissue contraction.

Until the tissue defect is filled with cellular connective tissue, the defect remains at risk of continued or new infection, inflammation and/or severe contraction. Therefore, the quicker the defect can heal, the sooner the risk is removed. Thus, the use of active enamel substances according to the present invention represent means that can influence the rate of connective tissue filling and organization and favorably influence the healing capacity of radiated and/or non-radiated connective tissues. Furthermore, as almost all tissue repair processes include the early connective tissue formation, a stimulation of this and the subsequent processes are also contemplated to improve the quality and quantity of tissue defect filling.

In the present context, the term "clinical healing" is used to denote a situation wherein no tissue interruption can be visually observed and only discrete signs of inflammation are present, such as a light redness or a discretely swollen tissue. In addition, no complaints of pain are present when the organ is relaxed or untouched.

As mentioned above, the invention relates to the use of enamel matrix, enamel matrix derivatives and/or enamel matrix proteins as an agent for stimulation of connective tissue growth, i.e. as an agent that accelerates, stimulates and/or promotes the growth of connective tissue cells. Accordingly, an important aspect is the use of an active enamel substance as a repair agent to prevent wound contraction, both surgical and radiation induced. Furthermore, secondarily to the biological effect, the administration of active enamel substances will render pain relief, because of a more rapid filling process of the defect and/or tissue-cavity and less wound contraction.

The enamel matrix, enamel matrix derivatives and/or enamel matrix proteins may be applied either directly into the soft tissue defect prior to suturing or it may be injected into the wound cavity after suturing. The volume/amount of enamel matrix, enamel matrix derivatives and/or enamel matrix proteins applied will differ from case to case and tissue to tissue, but generally, the therapy will aim at replacing the volume of the lost tissue. However, in cases where an increase or decrease of the volume of a tissue or body part, e.g. a breast, is desirable, the enamel matrix, enamel matrix derivatives and/or enamel matrix proteins may be applied in surplus or deficit to acquire the desired outcome. The active enamel substance may be used as such, or may be used in a suitable preparation or pharmaceutical composition.

The present inventors have in experiments with cultured dermal fibroblasts shown that cells that have received therapeutic dosages of ionising radiation can be stimulated with EMDOGAIN® (BIORA AB, Sweden) to replicate and grow almost at the speed of normal untreated cells. The ability of radiated cells to recover from the damage and to restore normal functions is crucial if contraction complications are to be avoided following cancer surgery and radiation therapy. Thus, the observation that active enamel substances can induce such beneficial changes in radiated fibroblasts proves the concept of the present invention.

Moreover, the inventors have found that active enamel substances have the ability to stimulate fibroblast invasion, proliferation and growth. Furthermore, there are indications that the application of active enamel substances leads to improved defect fill that reduces post operation and post radiation contractions in the defect. Also, the inventors have observed that the inflammation stage is shortened and the typical signs such as warmth, redness, oedema and pain are less noticeable, and that new tissue is formed more rapidly after application of active enamel substances. Thus, the observed time for wound healing (e.g. after surgery) is significantly shortened as compared to surgery without the use of active enamel substances.

Interestingly, the inventors have also observed that various cell cultures of fibroblasts (embryonic, dermal, derived from the periodontal ligament, fish fin or bird skin), produce twice as much transforming growth factor (TGF-$\beta$1) when stimulated with EMDOGAIN® (BIORA AB, SWEDEN), compared to non-stimulated cultures. As TGF-$\beta$1 is considered to be of central importance in the neogenesis and reorganization of connective tissue, these findings further support the concept of the present invention.

Significant tissue loss or defect following trauma or cytoreductive surgery normally produces cavities at the location of the removed tissue. These cavities usually fill with fluid and/or fibrous, dense scar tissue, causing the function and appearance of the remaining tissue to be severely impaired. If normal connective tissue growth is induced to fill such cavities, it dramatically improves the functional and esthetical outcome of cytoreductive surgery and trauma treatment.

The preparation of an active enamel substance according to the present invention is effective for treating a wide variety of different types and sizes of wounds. Regeneration of experimentally provoked periodontal wounds have previously been described by the inventors and is not intended to be within the scope of the present invention, neither is healing of wounds in skin or mucous membranes.

In the present context the terms "wound cavity", "tissue cavity" and "tissue defects" denote an internal bodily injury with disruption of the normal integrity of tissue structures that follows from a procedure and/or trauma that involves removal and/or loss of a significant amount of tissue from the body or a body part. The term is also intended to encompass the terms "surgical lesions", "necrosis", "abscesses", "mucocele", "cysts", "fistulas", "excavations", "alveola" and all other terms used to describe abnormal cavities within the human body or tissue.

A deep cavity-shaped wound is in the present context clearly defined in contrast to a shallow, open wound on the surface of a tissue, especially on the epidermis of a body, such as an abrasive-wound or a mucosal wound. A cavity-shaped wound creates a deep, substantially hollow space in the injured tissue and will either fill with fluids, scar tissue and/or collapse in the natural repair process.

Another way of classifying wound cavities or tissue defects is as i) significant tissue loss due to surgical incisions, radiation treatment, abrasions, lacerations, burns (chemical and thermal), donor site wounds and substantial bites, or as ii) significant tissue loss due to pathological conditions including ischemic ulcers, fistulae, neoplasms, tumours, hammartomas, infections, necrosis, and infarctions.

A "significant tissue loss" in the context of the present invention is meant to comprise an amount of tissue that is typically removed from an original tissue, for example but not exclusively, due to trauma or due to surgery, and that results in a deep wound in said tissue and/or that impairs function and/or appearance of said body part. A "significant tissue loss" in the context of the present invention will ultimately lead to scarring.

In one embodiment of the invention, significant tissue loss comprises e.g. the loss of at least 5% of weight of tissue, compared to the original weight of an organ or body part. Such a loss will in this context comprise a reduction of tissue mass of between 5% and 75%, such as between at least 5%, 5.5%, 6%, 6.5%, 7%, 7.5%, 8%, 8.5%, 9%, 9.5%, 10%, 11%, 12%, 13%, 14%, 15%, 16%, 17%, 18%, 19% or at least between 20% and 75%. In another embodiment of the present invention, the tissue loss comprises a reduction of tissue weight of at least 25%, such as at least 30%, 35%, 40%, 45%, 50%, 55%, 60%, 65%, 70%, 75%, 80%, or at least 85%.

In an especially preferred embodiment of this invention, the use of an active enamel substance for the preparation of a pharmaceutical or cosmetic composition for filling a tissue cavity and/or defect that is characterised by a substantial tissue loss is comprised, wherein the tissue loss is due to the surgical removal of a tumour and/or post surgical treatment with radiation therapy. In this specific embodiment, "significant tissue loss" in the context of the present invention is meant to comprise an amount of tissue ranging between about 1 ml–250 ml. Such a range will thus include an amount of tissue of about 1 ml, 1.25 ml, 1.5 ml, 2 ml, 2.25 ml, 2.5 ml, 2.75 ml, 3 ml, 3.25 ml, 3.5 ml, 3.75 ml, 4 ml, 4.25 ml, 4.5 ml, 4.75 ml, 5 ml, 5.25 ml, 5.5 ml, 5.75 ml, 6 ml, 6.25 ml, 6.5 ml, 6.75 ml, 7 ml, 7.25 ml, 7.5 ml, 7.75 ml, 8 ml, 8.25 ml, 8.5 ml, 8.75 ml, 9 ml, 9.25 ml, 9.5 ml, 9.75 ml, 10 ml, 15 ml, 20 ml, 25 ml, 50 ml, 75 ml, 100 ml, 150 ml, 200 ml or 250 ml.

In certain embodiments, wherein the tissue loss is e.g. due to the surgical removal of the majority of an organ or body part and/or a large tumour, the amount of tissue will of course include even larger volumes than 250 ml, such as between at least 250 ml and 500 ml, depending on the original size of the organ or body part and/or tumour.

The kinds of tissue cavities to be treated according to the invention include diverse orbital cavity or periorbital soft tissue and bony defects due to trauma, removal of benign or malignant neoplasms, tumours of the head and neck, abdomen and/or the extremities, particularly ovarian cancer and/or prostate cancer. They further comprise closed abdominal wounds, cavity wounds with negative pressure, penetrating thoracic and abdominal trauma wounds and/or abdominal gunshot injuries.

In the present context, a "tumour" stands for any new-growth of tissue in which the multiplication of cells is uncontrolled and progressive. The term "tumour" is herein equivalent to "neoplasm".

The invention comprises the use of an active enamel substance for the preparation of a pharmaceutical or cosmetic composition for filling a wound cavity and/or tissue defect that is due to surgical removal of primary and/or metastatic solid tumors and carcinomas of the breast, colon, rectum, lung, oropharynx, hypopharynx, esophagus, stomach, pancreas, liver, gallbladder, bile duct, small intestine, urinary tract including kidney, bladder and urothelium, female genital tract including cervix, uterus, ovaries, choriocarcinoma and gestational trophoblastic disease, male genital tract including prostate, seminal vesicles, testes and germ cell tumors, endocrine glands including thyroid, adrenal, and pituitary, skin including hemangiomas, melanomas, sarcoma arising from bone or soft tissues and Kaposi's sarcoma, tumors of the head, nerves, eyes, and meninges including astsrocytomas, gliomas, glioblastomas, retinoblastomas, neuromas, neuroblastomas, Schwannomas and meningiomas, solid tumors arising from hematopoietic malignancies such as leukemias and including chloromas, plasmacytomas, placques and tumors of mycosis fungoides, and cutaneous T-cell lymphoma/leukemia and/or lymphomas including both Hodgkin's and non-Hodgkin's lymphoma's.

In one embodiment of the present invention, tissue removed by resection during surgery includes not only tissue suspected by the surgeon of being neoplastic, but also includes an amount of healthy tissue taken because the precise tumour margins can not be ascertained by the surgeon. Coupled with the devastating risk of not removing neoplastic tissue resulting in tumour recurrence, surgical protocol dictates that healthy tissue is taken in order to ensure the removal of neoplastic tissue. Of course, the final determination as to whether the resected tissue is malignant falls to the pathologist who receives the tissue removed during the surgical procedure.

The present invention further relates to the use of an active enamel substance for the preparation of a pharmaceutical composition for a reconstruction that can be a post-mastectomy procedure, a post-traumatic procedure, or a procedure done to enlarge or decrease the volume of a breast. A reconstruction can be contemporaneous with a mastectomy or can be delayed, taking place over one or more post-mastectomy surgical procedures. In accordance with the invention, a delayed procedure comprises: a multistage procedure where a mastectomy is performed with contemporaneous placement of an expander, and a subsequent procedure when the reconstruction is performed; a mastectomy; a subsequent procedure when an expander is placed, and a subsequent procedure when reconstruction is performed; revisions to a previous reconstruction; or, the placing or modifying of breast implant materials that comprise a pharmaceutical composition according to the present invention.

Thus, the invention provides means for total and/or partial breast reconstruction that is either delayed or immediate. With an immediate reconstruction, the patient does not experience a mastectomy deformity and accompanying emotional trauma; however, for many women a delayed reconstruction is medically indicated. For patients who have undergone a standard modified radical mastectomy, delayed autologous reconstruction is accomplished after expansion of the skin envelope.

By use of preferred embodiments, a breast reconstruction according to the present invention can be performed on both breasts. Thus, if a subsequent breast cancer occurs in the contralateral breast, the same procedure can be performed. Alternatively, if a bilateral breast cancer is present, one or both breasts can be reconstructed with this technique.

As used herein, a "substantially circumareolar incision" comprises an incision that circumscribes at the perimeter of the nipple-areolar complex; in instances where a breast reduction and/or a nipple-areolar repositioning is to be performed, an incision that circumscribes at the perimeter of the nipple-areolar complex and includes additional breast skin; and, an incision that approximates the areolar perimeter yet is within the area of the areola. Preferably, particularly for immediate embodiments of the invention, the circumareolar incision closely corresponds to the perimeter of the areola, and is at or within the margin of the areola. A substantially circumareolar incision also comprises radial or wedge skin incisions at the border of the areola. Radial or wedge skin incisions at the border of the areola are less ideal since they create scarring that does not correspond to a natural tissue plane.

Advantageously, a reconstructed breast produced in accordance with the present invention has better contour and projection than reconstructed breasts that resulted from procedures well known to the skilled artisan.

Preferred embodiments of the procedure of the present invention are performed following a circumareolar mastectomy. A circumareolar mastectomy eliminates the transverse mastectomy scar that was a consequence of prior reconstruction procedures. To make most advantageous use of a circumareolar mastectomy, it is preferred that the surgeon limit any biopsy and subsequent mastectomy skin excision to the region of the nipple-areolar complex. When the skin excision in a mastectomy is limited to the region of the nipple-areolar complex, the skin envelope of the breast is completely preserved. Since the biopsy incision is generally removed at the time of the mastectomy, biopsy incisions outside the region of the areola often necessitate a non-preferably large skin incision on the breast skin envelope. With a large skin incision, the mastectomy scar is not camouflaged at the border of the areola, and the reconstructed breast is less likely to have a normal contour.

A mastectomy excision through a substantially circumareolar incision that is larger than the areolar perimeter can be performed in accordance with the invention, particularly for patients for whom a breast reduction and/or nipple-areolar repositioning is indicated; for such patients, a "substantially circumareolar incision" comprises an incision that corresponds to the perimeter of the areola and comprises an incision that corresponds to a standard pattern reduction or repositioning incision. In general, if a skin resection extends beyond the perimeter of the nipple-areolar complex, the resulting mastectomy scar is more readily apparent.

Alternatively, yet also in accordance with the present invention, a variable amount of areola may be left with the breast skin.

Radiation therapy is known to those skilled in the art to be less distorting if performed after a breast reconstruction. Patients necessitating postoperative radiation therapy will be candidates for the use of the present invention. The use will alter the patient's post-operative prognosis favourably. Size or stage of the breast cancer will not limit applicability of the procedure. If a modified radical mastectomy with a large elliptical skin excision is indicated, a delayed reconstruction in accordance with the invention is generally used.

Additionally to the use in breast surgery, the present invention further relates to the use of an active enamel substance for the preparation of a pharmaceutical composition for reconstruction or for guided connective tissue growth after vaginal, urinal and/or anal surgery or surgery on urine bladder, womb or intestines.

In the scope of the present invention are also other uses for repairing soft tissue defects, such as soft tissue defects resulting from incisional hernias and soft tissue defects resulting from extirpative tumour surgery. Other applications of the present invention include laparoscopic inguinal hernia repair, standard inguinal hernia repair, umbilical hernia repair, paracolostomy hernia repair, femora hernia repair, lumbar hernia repair, and the repair of other abdominal wall defects, thoracic wall defects and diaphragmatic hernias and defects.

In yet another embodiment, the present invention relates to the use of an active enamel substance for the preparation of a pharmaceutical or cosmetic composition for the enlargement of a breast or any other soft tissue of a mammal, wherein a certain amount of said composition, is inserted into a mammalian tissue without any prior loss of tissue. This embodiment incorporates the use of an active enamel substance for purely cosmetic reasons and is not limited to a post-surgical treatment of a tumour, such as e.g. breast cancer. In this context, the scope of the invention therefore relates to cosmetic methods for treating a human being with an active enamel substance for stimulating the neogenesis of soft tissue, characterised by inserting or injecting a suitable pharmaceutical composition comprising active enamel substances, such as e.g. EMDOGAIN® (BIORA AB, Sweden) into the organ and/or body part, wherein cosmetical enlargement or filling is desired.

Enamel matrix is a precursor to enamel and may be obtained from any relevant natural source, i.e. a mammal in which teeth are under development. A suitable source is developing teeth from slaughtered animals such as, e.g., calves, pigs or lambs. Another source is e.g. fish skin.

Enamel matrix can be prepared from developing teeth as described previously (EP-B-0 337 967 and EP-B-0 263 086). The enamel matrix is scraped off and enamel matrix derivatives are prepared, e.g. by extraction with aqueous solution such as a buffer, a dilute acid or base or a water/solvent mixture, followed by size exclusion, desalting or other purification steps, followed by freeze-drying. Enzymes may alternatively be deactivated by treatment with heat or solvents, in which case the derivatives may be stored in liquid form without freeze-drying.

As an alternative source of the enamel matrix derivatives or proteins one may also use generally applicable synthetic routes, well known to a person skilled in the art, or use cultivated eukaryotic and/or prokaryotic cells modified by DNA-techniques. The enamel matrix proteins may thus be of recombinant origin and alternatively genetically modified (see, e.g., Sambrook, J. et al.: Molecular Cloning, Cold Spring Harbor Laboratory Press, 1989).

In the present context, enamel matrix derivatives are derivatives of enamel matrix which include one or several enamel matrix proteins or parts of such proteins, produced naturally by alternate splicing or processing, or by either enzymatic or chemical cleavage of a natural length protein, or by synthesis of polypeptides in vitro or in vivo (recombinant DNA methods or cultivation of diploid cells). Enamel matrix protein derivatives also include enamel matrix related polypeptides or proteins. The polypeptides or proteins may be bound to a suitable biodegradable carrier molecule, such as polyamine acids or polysaccharides, or combinations thereof. Furthermore, the term enamel matrix derivatives also encompass synthetic analogous substances.

Proteins are biological macromolecules constituted by amino acid residues linked together by peptide bonds. Proteins, as linear polymers of amino acids, are also called polypeptides. Typically, proteins have 50–800 amino acid residues and hence have molecular weights in the range of from about 6,000 to about several hundred thousand Dalton or more. Small proteins are called peptides or oligopeptides.

Enamel matrix proteins are proteins that normally are present in enamel matrix, i.e. the precursor for enamel (Ten Cate: Oral Histology, 1994; Robinson: Eur. J. Oral Science, January 1998, 106 Suppl. 1:282–91), or proteins which can be obtained by cleavage of such proteins. In general, such proteins have a molecular weight below 120,000 Dalton and include amelogenins, non-amelogenins, proline-rich non-amelogenins and tuftelins.

Examples of proteins for use according to the invention are amelogenins, proline-rich non-amelogenins, tuftelin, tuft proteins, serum proteins, salivary proteins, ameloblastin, sheathlin, and derivatives thereof, and mixtures thereof. A preparation containing an active enamel substance for use according to the invention may also contain at least two of the aforementioned proteinaceous substances. Moreover, other proteins for use according to the invention are found in the marketed product EMDOGAIN® (BIORA AB, Sweden).

EMDOGAIN® (BIORA AB, S-205 12 Malmö, Sweden) contains 30 mg Enamel Matrix protein, heated for 3 hours at about 80° C. in order to inactivate residual proteases, and 1 ml Vehicle Solution (Propylene Glycol Alginate), which are mixed prior to application, unless the protein and the Vehicle are tested separately. The weight ratio is about 80/8/12 between the main protein peaks at 20, 14 and 5 kDa, respectively.

In general, the major proteins of an enamel matrix are known as amelogenins. They constitute about 90% w/w of the matrix proteins. The remaining 10% w/w includes proline-rich non-amelogenins, tuftelin, tuft proteins, serum proteins and at least one salivary protein; however, other proteins may also be present such as, e.g., amelin (ameloblastin, sheathlin) which have been identified in association with enamel matrix. Furthermore, the various proteins may be synthesised and/or processed in several different sizes (i.e. different molecular weights). Thus, the dominating proteins in enamel matrix, amelogenins, have been found to exist in several different sizes that together form supramolecular aggregates. They are markedly hydrophobic substances that under physiologically conditions form aggregates. They may carry or be carriers for other proteins or peptides.

Other protein substances are also contemplated to be suitable for use according to the present invention. Examples include proteins such as proline-rich proteins and polyproline. Other examples of substances that are contemplated to be suitable for use according to the present invention are aggregates of such proteins, of enamel matrix derivatives and/or of enamel matrix proteins as well as metabolites of enamel matrix, enamel matrix derivatives and enamel matrix proteins. The metabolites may be of any size ranging from the size of proteins to that of short peptides.

As mentioned above, the proteins, polypeptides or peptides for use according to the invention typically have a molecular weight of at the most about 120 kDa such as, e.g., at the most 100 kDa, 90 kDa, 80 kDa, 70 kDa or 60 kDa as determined by SDS PAGE electrophoresis.

The proteins for use according to the invention are normally presented in the form of a preparation, wherein the protein content of the active enamel substance in the preparation is in a range of from about 0.05% w/w to 100% w/w such as, e.g., about 5–99% w/w, about 10–95% w/w, about 15–90% w/w, about 20–90% w/w, about 30–90% w/w, about 40–85% w/w, about 50–80% w/w, about 60–70% w/w, about 70–90% w/w, or about 80–90% w/w.

A preparation of an active enamel substance for use according to the invention may also contain a mixture of active enamel substances with different molecular weights.

The proteins of an enamel matrix can be divided into a high molecular weight part and a low molecular weight part, and it has been found that a well-defined fraction of enamel matrix proteins possesses valuable properties with respect to treatment of periodontal defects (i.e. periodontal wounds). This fraction contains acetic acid extractable proteins generally referred to as amelogenins and constitutes the low molecular weight part of an enamel matrix (cf. EP-B-0 337 967 and EP-B-0 263 086).

The low molecular weight part of an enamel matrix has a suitable activity for inducing binding between hard tissues in periodontal defects. In the present context, however, the active proteins are not restricted to the low molecular weight part of an enamel matrix. At present, preferred proteins include enamel matrix proteins such as amelogenin, tuftelin, etc. with molecular weights (as measured in vitro with SDS-PAGE) below about 60,000 Dalton but proteins having a molecular weight above 60,000 Dalton have also promising properties as candidates for promoting connective tissue growth.

Accordingly, it is contemplated that the active enamel substance for use according to the invention has a molecular weight of up to about 40,000 such as, e.g. a molecular weight of between about 5,000 and about 25,000.

By separating the proteins, e.g. by precipitation, ion-exchange chromatography, preparative electrophoresis, gel permeation chromatography, reversed phase chromatography or affinity chromatography, the different molecular weight amelogenins can be purified.

The combination of molecular weight amelogenins may be varied, from a dominating 20 kDa compound to an aggregate of amelogenins with many different molecular weights between 40 and 5 kDa, and to a dominating 5 kDa compound. Other enamel matrix proteins such as tuftelin or proteolytic enzymes normally found in enamel matrix can be added and carried by the amelogenin aggregate.

In general, the enamel matrix, enamel matrix derivatives and enamel matrix proteins are hydrophobic substances, i.e. less soluble in water, especially at increased temperatures. In general, these proteins are soluble at non-physiological pH values and at a low temperature such as about 4–20° C., while they will aggregate and precipitate at body temperature (35–37° C.) and neutral pH.

The enamel matrix, enamel matrix derivatives and/or enamel matrix proteins for use according to the invention comprise an active enamel substance, wherein at least a part is in the form of aggregates or after application in vivo is capable of forming aggregates. The particle size of the aggregates is in a range of from about 20 nm to about 1 μm.

In accordance to the present invention, an active enamel substance may be used together with other active drug substances such as, e.g. anti-bacterial, anti-inflammatory, antiviral, antifungal substances or in combination with local chemotherapy, inducers of apoptosis, growth factors such as, e.g., TGFβ, PDGF, IGF, FGF, EGF, keratinocyte growth factor or peptide analogues thereof. Enzymes—either inherently present in the enamel matrix or preparation thereof or added—may also be used in combination with an enamel matrix, enamel matrix derivative and/or enamel matrix protein, especially proteases.

A preparation of an active enamel substance is normally formulated as a pharmaceutical or cosmetic composition. Such a composition may of course consist of the proteinaceous preparation or it may further comprise a pharmaceutically or cosmetically acceptable excipient. Especially suitable excipients for use in pharmaceutic or cosmetic compositions are propylene glycol alginate, or hyaluronic acid or salts or derivatives thereof.

In the following, examples of suitable compositions containing an active enamel substance(s) are given. Depending on the use of the active enamel substance(s), a composition may be a pharmaceutical or a cosmetic composition. In the following the term "pharmaceutical composition" is also intended to embrace cosmetic compositions as well as compositions belonging to the so-called grey area between pharmaceuticals and cosmetics, namely cosmeceuticals.

For the administration to an individual (an animal or a human), an active enamel substances and/or a preparation thereof is preferably formulated into a pharmaceutical composition containing the active enamel substance and, optionally, one or more pharmaceutically acceptable excipients.

A composition comprising the active enamel substance to be administered may be adapted for administration by any suitable route, e.g. by topical administration through a syringe, or by administration to a tissue cavity through a hose or draining device. Furthermore, a composition may be adapted to administration in connection with surgery, e.g. in connection with incision within the body in order to promote repair and filling of deep cavity-shaped wounds, substantial tissue losses after surgery and tissue defects.

As mentioned above, a composition of the active enamel substance(s) may be suitable for use during surgery, e.g. for local application (e.g. in a breast or in the abdominal wall) in the form of a gel, film or dry pellet to induce fibroblast invasion, proliferation and growth.

The compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

As mentioned above, the application of a composition comprising an active enamel substance is intended for inducing and stimulating connective tissue cell invasion, proliferation and growth as part of a repair process following significant removal or loss of tissue. Other applications may of course also be relevant such as application directly in or into a deep wound or other substantial tissue defects.

A pharmaceutical composition comprising an active enamel substance serves as a drug delivery system. In the present context the term "drug delivery system" denotes a pharmaceutical composition (a pharmaceutical formulation or a dosage form) that upon administration presents the active substance to the body of a human or an animal. Thus, the term "drug delivery system" embraces plain pharmaceutical compositions such as, e.g., creams, ointments, liquids, powders, tablets, etc. as well as more sophisticated formulations such as dressings, devices, templates, smart-gels, grafts etc.

Apart from the active enamel substance, a pharmaceutical composition for use according to the invention may comprise pharmaceutically or cosmetically acceptable excipients.

A pharmaceutically or cosmetically acceptable excipient is a substance that is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

Whether a pharmaceutically acceptable excipient is suitable for use in a pharmaceutical composition is generally dependent on which kind of dosage form is chosen for use for a particular kind of wound. In the following examples of suitable pharmaceutically acceptable excipients are given for use in different kinds of compositions for use according to the invention.

In the following is given a review on relevant pharmaceutical compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

The choice of pharmaceutically acceptable excipient(s) in a composition for use according the invention and the optimum concentration thereof cannot generally be predicted and must be determined on the basis of an experimental evaluation of the final composition. However, a person skilled in the art of pharmaceutical formulation can find guidance in e.g., "Remington's Pharmaceutical Sciences", 18th Edition, Mack Publishing Company, Easton, 1990.

For application into the tissue defect, the compositions for use according to the invention may contain conventionally non-toxic pharmaceutically acceptable carriers and excipients including microspheres and liposomes.

The compositions for use according to the invention include all kinds of solid, semi-solid and fluid compositions. Compositions of particular relevance are e.g. pastes, ointments, hydrophilic ointments, creams, gels, hydrogels, solutions, emulsions, suspensions, powders, films, foams, pads, sponges (e.g. collagen sponges) and transdermal delivery systems.

The pharmaceutically acceptable excipients may include solvents, buffering agents, preservatives, humectants, chelating agents, antioxidants, stabilizers, emulsifying agents, suspending agents, gel-forming agents, ointment bases, penetration enhancers, perfumes, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rape seed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogen phosphoric acid, diethylamine etc.

Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of chelating agents are sodium EDTA and citric acid.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol aginate.

Examples of hydrophobic or water-emulsifying ointment bases are paraffins, vegetable oils, animal fats, synthetic glycerides, waxes, lanolin, and liquid polyalkylsiloxanes.

Examples of hydrophilic ointment bases are solid macrogols (polyethylene glycols).

Examples of powder components are: alginate, collagen, lactose, powder which is able to form a gel when applied to a wound (absorbs liquid/wound exudate). Normally, powders intended for application on large open wounds must be sterile and the particles present must be micronized.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and kitosans.

The compositions mentioned above for topical administration are most suitably for application directly into tissue defects or by any convenient route of administration.

Compositions which have proved to be of importance in connection with topical application are those which have tixothropic properties, i.e. the viscosity of the composition is affected e.g. by shaking or stirring so that the viscosity of the composition at the time of administration can be reduced and when the composition has been applied, the viscosity increases so that the composition remains at the application site.

Suitable compositions for use according to the invention may also be presented in the form of suspensions, emulsions or dispersions. Such compositions contain the active enamel substance in admixture with a dispersing or wetting agent, suspending agent, and/or one or more preservatives and other pharmaceutically acceptable excipients. Such compositions may also be suitable for use in the delivery of the active enamel substance to e.g. an intact or damaged tissue with a cavity like defect.

Suitable dispersing or wetting agents are, e.g., naturally occurring phosphatides, e.g., lecithin, or soybean lecithin; condensation products of ethylene oxide with e.g. a fatty acid, a long chain aliphatic alcohol, or a partial ester derived from fatty acids and a hexitol or a hexitol anhydride, e.g. polyoxyethylene stearate, polyoxyethylene sorbitol monooleate, polyoxyethylene sorbitan monooleate, etc.

Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g. Avicel® RC 591, methylcellulose); alginates and kitosans such as, e.g., sodium alginate, etc.

Suitable examples of preservatives for use in compositions according to the invention are the same as those mentioned above.

In a pharmaceutical composition for use according to the invention on skin or mucosa, an active enamel substance is generally present in a concentration ranging from about 0.01% to about 99.9% w/w. The amount of composition applied will normally result in an amount of total protein per $cm^2$ wound/tissue-defect area, corresponding to from about 0.01 $mg/cm^2$ to about 20 $mg/cm^2$ such as from about 0.1 $mg/cm^2$ to about 15 $mg/cm^2$.

The amount applied of the composition depends on the concentration of the active enamel substance in the composition and of the release rate of the active enamel substance from the composition, but is generally in a range corresponding to at the most about 15–20 $mg/cm^2$.

In those cases where the active enamel substance is administered in the form of a fluid composition, the concentration of the active enamel substance in the composition is in a range corresponding to from about 0.1 to about 50 mg/ml. Higher formulation/dosages are in some cases desirable and can also be obtained such as of at least about 50 mg/ml.

The concentration of the active enamel substance in a pharmaceutical composition depends on the specific enamel substance, its potency, the severity of the tissue loss or defect to be prevented or treated, and the age and condition of the patient. Methods applicable to selecting relevant concentrations of the active enamel substance in the pharmaceutical composition are well known to a person skilled in the art and may be performed according to established guidelines for good clinical practice (GCP) or Investigational New Drug Exemption ("IND") regulations as described in e.g. International Standard ISO/DIS 14155 Clinical investigation of medical devices, 1994 and ICH (International Committee for Harmonisation): Harmonised tripartite guideline for good clinical practice, Brookwood Medical Publications, Ltd, Surrey, UK, 1996. A person skilled in the art would, by use of the methods described in standard textbooks, guidelines and regulations as described above as well as common general knowledge within the field, be able to select the exact dosage regimen to be implemented for any active enamel substance and/or selected other active substances and dosage form using merely routine experimentation procedures.

As will be understood, details and particulars concerning the use of an active enamel substance for the induction and stimulation of connective tissue cell invasion, proliferation and growth will be the same as or analogous to the details and particulars concerning the other use aspects (anti scarring and contraction resistance) and the method aspects discussed above, and this means that wherever appropriate, the statements above concerning an active enamel substance, a preparation containing an active enamel substance, a pharmaceutical composition containing an active enamel substance, preparation of i) an active enamel substance, ii) a preparation containing an active enamel substance, iii) a pharmaceutical composition containing an active enamel substance, as well as improved properties and uses apply mutatis mutandis to all aspects of the invention.

The observation, that enamel matrix is formed and temporarily present during root and root cementum formation can explain how application of enamel matrix, enamel matrix derivatives and/or enamel matrix proteins promotes the regeneration of periodontal tissue.

However, the observation underlying the present invention that enamel matrix, enamel matrix derivatives and/or enamel matrix proteins also have a positive effect on invasion, proliferation and growth of connective tissue cells is very surprising. The same applies to the observations with respect to the reduced scarring and contraction observed in treated defects. As demonstrated in the experimental section herein, the active enamel substance aggregates and revitalises radiated fibroblasts cells and initiates fibroblast cell migration, replication and growth.

Experiments

The therapeutic and/or prophylactic activity of active enamel substances may of course be evidenced by in vivo tests, using experimental animals or humans. However, an indication of the efficacy and/or activity of enamel matrix, enamel matrix derivatives and/or enamel matrix proteins can be obtained by performing relatively simple in vitro tests such as, e.g., tests involving cell cultures.

Furthermore, there are several parameters that may be employed in order to evaluate a wound healing effect. These include:

Ultra-sound analysis of treated tissues

Magnet resonance imaging (MR)

Histopathology/cytology (microscopic evaluation of wound tissues and fluids)

Scintigraphy (radionuclide imaging of wound tissue)

EXAMPLE 1

Investigation of growth behaviour of dermal fibroblasts cultured in the presence of enamel matrix derivative.

The purpose of this example is to show the capacity of enamel matrix derivative to induce and stimulate dermal fibroblast cell attachment, replication and growth.

Cell Isolation and Culture Conditions

Human dermal fibroblasts, obtained from ATTC, were cultured from healthy dermal tissues from young healthy volunteering individuals. Cultures were maintained in DMEM with 10% foetal bovine serum. EMD, EMDOGAIN®(BIORA AB, Sweden), was added prior to commencement of cell cultures, by coating charged plastic culture dishes with a 0.5 mg/ml EMD solution in 0.1% HAc in PBS overnight. In addition, the medium was supplemented with 100 µg EMD per milliliter. The EMD concentrations were chosen on the basis of pilot experiments with cultured cells indicating that optimal growth occurred at these values, and that cell growth did not benefit from further addition of EMD. There were no changes of media during the five to seven day observation period of this study. All experiments commenced with 50,000 cells per milliliter of culture medium.

Cell Attachment

To assess the cell attachment rate during the first four hours after seeding, 100,000 cells were cultured on EMD coated surfaces for 30, 60, 120 or 240 minutes before the cultures were vigorously washed with PBS to remove all unattached cells. The washing solution was centrifuged and the numbers of unattached cells were analysed using a Bürker chamber. The attached cells were then removed from the surface by trypsinisation and counted in the same way for control. Uncoated dishes were used as negative control.

Cell Culture Densities

Cells were seeded and maintained in cultures with or without EMD for 24, 48, 72, 96 or 120 hours. Cultures were then carefully washed with PBS and the number of attached cells per square millimeter was calculated in the microscope using a fixed grid.

Cell Metabolism

Cells were cultured for 24, 48, 72, 96, 120 or 144 hours and then given a 4-hour pulse of 50 µCi [$^{35}$S]methionine (Cell culture grade, Amersham Pharmacia Biotech). The cultures were then washed with PBS and the cells were removed by trypsinisation. The cells were then washed again, centrifuged and 200 µl of each cell pellet were dissolved in UniverSol™ liquid scintillation cocktail (ICN Biomedicals Inc.) and counted two times 300 seconds in a Packard Tricarb scintillation counter.

Nucleic Acid Synthesis

Nucleic acid synthesis in cells cultures 24, 48, 72 or 96 hours was assessed by colorimetric analysis at 370 nm following a 4-hour pulse with BrdU using the Boehringer Mannheim Cell PROLIFERATION ELISA, BRDU KIT® (Cat. No. 164229). During the pulse, the pyrimidine analog BrdU was incorporated in place of thymidine into the newly synthesized DNA of proliferating cells. At the end of the pulse the cells were washed, fixed and denatured and the amount of incorporated BrdU was measured by ELISA utilizing an anti-BrdU peroxidase conjugated antibody.

Results

Figure 2:
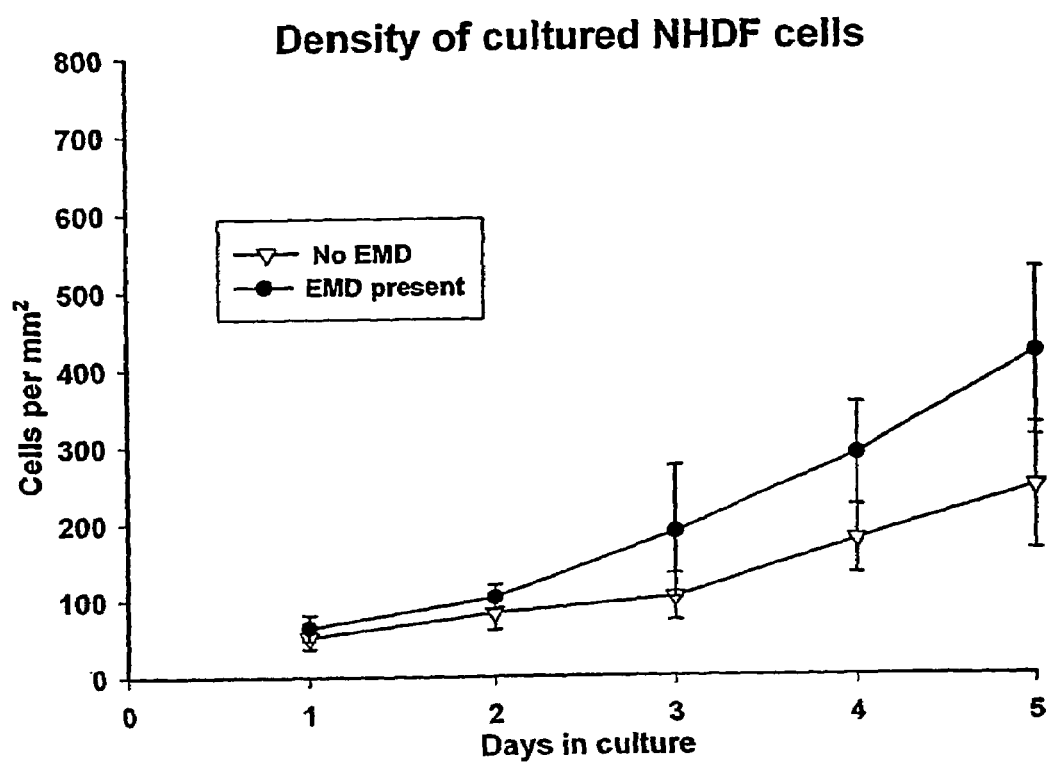

The experiments showed that fibroblast cell attachment rate during the first hours after seeding is nearly five times more efficient when the surface of the culture dish is coated with EMD (FIG. 1). Cell density in the cultures increased faster when EMD was present (FIG. 2). The general trend was that cultures growing in the presence of EMD got a one-day lead, reaching confluence after four days in culture, one day ahead of the control cells. The metabolic rate of fibroblast cells also increased on a per cell basis in cultures seeded on EMD as compared to control cultures (FIG. 3). This increase in [$^{35}$S]methionine utilisation was higher than the observed change in growth rate alone.

In pulse-chase experiments with the thymidine analogue bromodeoxyuridine (BrdU) fibroblast cell cultures showed an increased DNA synthesis in the presence of EMD (FIG. 4). The results prove that EMD stimulates fibroblast proliferation and differentiation. The fibroblasts in the experiment attached to the dishes and grew quicker than those in the uncoated dishes, their metabolism was enhanced and they most probably expressed cell-specific proteins.

EXAMPLE 2

Investigation of recovery of fibroblast cells exposed to ionising radiation by application of enamel matrix derivative.

The purpose of this example is to show the ability of enamel matrix derivative to revitalise fibroblast cells that have been exposed to ionising radiation.

Cell Isolation and Culture Conditions

Human dermal fibroblasts, obtained from ATTC, were cultured from healthy dermal tissues from young healthy volunteering individuals. Cultures were maintained in DMEM with 10% foetal bovine serum. EMD was added prior to commencement of cell cultures, by coating charged plastic culture dishes with a 0.5 mg/ml EMD solution in 0.10% HAc in PBS overnight. In addition, the medium was supplemented with 100 µg of EMD per milliliter. The EMD concentrations were chosen on the basis of pilot experiments with cultured cells indicating that optimal growth occurred at these values, and that cell growth did not benefit from further addition of EMD. There were no changes of media during the five to seven day observation period of this study. All experiments commenced with 50,000 cells per milliliter of culture medium.

Radiation Therapy

Confluent cultures of dermal fibroblast cells, cultured without EMD, received a gamma radiation dosage of 0, 1, 2, 5 10, 15 and 20 Grey. Immediately after radiation therapy, the cultures were split in two by trypsination and seeding according to standard operating procedures. One of the parallels was then cultured with 100 μg/ml EMD present in the medium, whereas the other was cultured without EMD as unstimulated control.

Cell Culture Densities

Cells were seeded and maintained in cultures with or without EMD for 24, 48, 72, 96 or 120 hours. Cultures were then carefully washed with PBS and the number of attached cells per square millimeter was calculated in the microscope using a fixed grid.

Results

Radiated cells growing in the presence of EMD increased their number twice as fast as unstimulated cultures (FIGS. 5A and 5B). This trend was true for all cultures, even though in general the growth potential of the cultured dermal fibroblasts decreased with increasing radiation dosages. The results demonstrate that EMD can revitalise radiated cultured dermal fibroblast cells, and that the presence of EMD proteins stimulates proliferation and growth of these cells also when basic cellular functions are impaired by radiation damage.

EXAMPLE 3

Investigation of soft tissue defect fill and prevention of scarring and tissue contraction after surgical removal of a breast tumour followed by radiation therapy.

The purpose of this example is to show the influence of active enamel substances on improvement of soft tissue defect fill and reduced tissue contraction after cytoreductive surgery and radiation therapy.

An active enamel substance may be applied either directly into a soft tissue defect prior to suturing or it may be injected into the wound cavity after suturing. The volume/amount of active enamel substances applied will differ from case to case and tissue to tissue, but mostly the therapy will aim at replacing the volume of the lost tissue. However, in cases where an increase or decrease of the volume of a tissue or body part, e.g. a breast, is desirable, the enamel matrix, enamel matrix derivatives and/or enamel matrix proteins may be applied in surplus or deficit to acquire the desired outcome. The active enamel substance may be used as such or may be used in a suitable preparation or pharmaceutical composition.

A patient with a diagnosed adenocarcinoma in the breast is submitted for surgical removal of the tumor according to standard aesthetic and surgical procedures. After resection of the tumor tissue, the mass of the removed tissue is estimated to about 5 ml. The wound cavity in the breast is then half closed by suturing at the incision, carefully avoiding pull, tension or contraction in the walls of the wound cavity. The wound cavity is then thoroughly rinsed with sterile saline to remove blood clots, cell debris and damaged tissue. After thoroughly draining the saline from the wound cavity, EMD in PGA in the form of EMDOGAIN® Gel (BIORA AB, Sweden) is injected into the wound cavity so that the whole of the cavity is filled (volume>5 ml). Finally, the wound cavity is closed by sutures at the incision site, taking care that the EMDOGAIN® Gel (BIORA AB, Sweden) remains in situ. No draining device is applied, and standard postoperative procedures and wound care are applied.

The patient is allowed to recover from surgery for two weeks before he/she is submitted to adjuvant radiation therapy of the treated breast. Prior to the radiation therapy, the wound healing is assessed by clinical examination, ultrasound and imaging in order to monitor connective tissue growth in the tissue defect. Clinical pictures and measurements of the size and location of the healing defect are recorded.

To ensure total eradication of malignant cells from the breast, the patient is submitted to local radiation therapy. The radiation dosage depends on the phenotype of the malignant cells (assessed by histology on tissue removed during surgery), the size of the breast and the condition of the patient (age, weight, systemic diseases etc.). The typical dosage ranges between 0.5 and 20 Gray. If considered necessary, radiation therapy is repeated until the patient is declared free from primary tumour cells.

Following the first radiation therapy, the patient is monitored every week the first four weeks and then every month the next six months, for connective tissue wound fill, tissue contractions and appearance. The healing process and cell invasion into the tissue defect is monitored by clinical measurements, palpation, photography, and/or ultra sound imaging. The patient is asked to fill in a questionnaire regarding postoperative discomfort and the progression of the healing. If possible, aspiration biopsies are obtained from the healing breast to assess the type and quantity of cellular ingrowth in the defect.

In the frequent normal cases without the use of EMD, the wound cavity starts to contract after the first radiation therapy. This is due to the removal of proliferating fibroblasts from the wound by radiation, leaving a cell poor dense connective tissue that shrinks as the wound organises. At six months, the wound contraction often is so severe that the patients prefer to have most of the breast removed and replaced by silicon inlays. Thus, conservative surgery in breasts scheduled for radiation therapy often fails. However, by application of EMD into the wound cavity prior to radiation therapy, a wound fill comprising cell rich, loose connective tissue that is less sensitive to radiation induced contraction is achieved. By reducing contraction in these wounds, the post radiation wound healing is improved and the need for additional corrective surgery and/or prosthesis treatment is significantly reduced.

LIST OF REFERENCES

1. Hammarström et al., 1997, Journal of Clinical Periodontology 24, 658–668
2. Lyngstadaas et al., 2000, Journal of Clinical Periodontology 27, 1–8
3. Ten Cate: Oral Histology, 1994;
4. Robinson: Eur. J. Oral Science, January 1998, 106 Suppl. 1:282–91
5. Janson, J-C & Rydén, L. (Eds.), Protein purification, VCH Publishers 1989
6. Fincham et al. in J. Struct. Biol. 1994 March–April; 112(2): 103–9 and in 3. Struct. Biol. 1995 July–August; 115(1): 50–9)

7. "Remington's Pharmaceutical Sciences" and "Encyclopedia of Pharmaceutical Technology", edited by Swarbrick, J. & J. C. Boylan, Marcel Dekker, Inc., New York, 1988
8. "Remington's Pharmaceutical Sciences", 18th Edition, Mack Publishing Company, Easton, 1990
9. International Standard ISO/DIS 14155 Clinical investigation of medical devices, 1994
10. Harmonised tripartite guideline for good clinical practice, Brookwood Medical Publications, Ltd, Surrey, UK, 1996
11. Harris, ELV & Angal, S., Protein purification methods—A practical approach, IRL Press, Oxford 1990
12. Sambrook, J. et al.: Molecular Cloning, Cold Spring Harbor Laboratory Press, 1989
13. Gestrelius S, Lyngstadaas SP, Hammarstrøm L. Emdogain—periodontal regeneration based on biomimicry. Clin Oral Invest 4:120–125, 2000

What is claimed is:

1. A pharmaceutical or cosmetic composition for filling a wound cavity and/or tissue defect resulting from a procedure and/or trauma following cytoreductive surgery, said composition comprising an active enamel substance, wherein the active enamel substance is enamel matrix, enamel matrix derivatives, or enamel matrix proteins.

2. The composition according to claim 1, wherein said composition stimulates cellular neogenesis in said wound cavity and/or tissue defect.

3. The composition according to claim 1, wherein said composition stimulates cellular proliferation, differentiation and/or maturation in said wound cavity and/or tissue defect.

4. The composition according to claim 3, wherein the stimulation is cell-type specific.

5. The composition according to claim 4, wherein the stimulation is cell-type specific for a cell from mesodermal and/or endodermal origin.

6. The composition according to claim 1, wherein the cavity or defect is caused by cytoreductive surgery.

7. The composition according to claim 1, wherein the cavity or defect is at least partly caused by radiation therapy.

8. The composition according to claim 1, wherein the cavity or defect is caused by a bodily injury, infection or trauma.

9. The composition according to claim 1, wherein the cavity or defect is caused by the surgical removal of a tumor selected from the group consisting of mammalian neoplasm, neck and head cancer, abdominal cancer, ovarian cancer, breast cancer and skin cancer.

10. The composition according to claim 1, wherein the cavity or defect is caused by the surgical removal of a breast tumor.

11. The composition according to claim 1, wherein the active enamel substance is selected from the group consisting of enamelins, amelogenins, non-amelogenins, proline-rich non-amelogenins, tuftelins, and mixtures thereof.

12. The composition according to claim 1, wherein the active enamel substance has a molecular weight that does not exceed about 120 kDa as determined by SDS PAGE electrophoresis.

13. The composition according to claim 1, wherein the active enamel substance has a molecular weight between about 60 kDa and 100 kDa as determined by SDS PAGE electrophoresis.

14. The composition according to claim 1, wherein the composition comprises a mixture of active enamel substances with different molecular weights.

15. The composition according to claim 1, wherein the active enamel substance comprises at least two substances selected from the group consisting of amelogenins, proline-rich non-amelogenins, tuftelins, tuft proteins, serum proteins, salivary proteins, ameloblastin, and sheathlin.

16. The composition according to claim 1, wherein the active enamel substance has a molecular weight of up to about 40,000.

17. The composition according to claim 1, wherein the active enamel substance has a molecular weight of between about 5,000 and about 25,000.

18. The composition according to claim 1, wherein the major part of the active enamel substance has a molecular weight of about 20 kDa.

19. The composition according to claim 1, wherein at least a part of the active enamel substance is in the form of aggregates or after application in vivo is capable of forming aggregates.

20. The composition according to claim 19, wherein the aggregates have a particle size of from about 20 nm to about 1 μm.

21. The composition according to claim 1, wherein the active enamel substance has a protein content in the composition in a range of from about 0.05% w/w to 100% w/w.

22. The composition according to claim 1, wherein the active enamel substance has a protein content in the composition in a range of from about 5% w/w to 99% w/w.

23. The composition according to claim 1, wherein the active enamel substance has a protein content in the composition in a range of from about 10–95% w/w.

24. The composition according to claim 1, wherein the active enamel substance has a protein content in the composition in a range of from about 15–90% w/w.

25. The composition according to claim 1, wherein the active enamel substance has a protein content in the composition in a range of from about 20–90% w/w.

26. The composition according to claim 1, wherein the active enamel substance has a protein content in the composition in a range of from about 30–90% w/w.

27. The composition according to claim 1, wherein the active enamel substance has a protein content in the composition in a range of from about 40–85% w/w.

28. The composition according to claim 1, wherein the active enamel substance has a protein content in the composition in a range of from about 50–80% w/w.

29. The composition according to claim 1, wherein the active enamel substance has a protein content in the composition in a range of from about 60–70% w/w.

30. The composition according to claim 1, wherein the active enamel substance has a protein content in the composition in a range of from about 70–90% w/w.

31. The composition according to claim 1, wherein the pharmaceutical composition further comprises a pharmaceutically acceptable excipient.

32. The composition according to claim 31, wherein the pharmaceutically acceptable excipient is propylene glycol alginate.

33. The composition according to claim 1, wherein the pharmaceutical composition comprises 68 mg of enamel matrix protein and 1 ml of vehicle solution.

34. A method for the treatment and/or reduction of scarring and/or wound contraction comprising administering an effective amount of a pharmaceutical or cosmetic composition for filling a wound cavity and/or tissue defect resulting from a procedure and/or trauma following cytoreductive surgery such that the scarring and/or wound contraction is treated and/or reduced, said composition comprising an active enamel substance, wherein the active enamel substance is enamel matrix, enamel matrix derivatives, or enamel matrix proteins.

35. A method according to claim 34, wherein the tissue is selected from the group consisting of breast tissue, lip tissue, abdominal wall tissue, facial tissue, neck tissue, tissue of the extremities, soft tissue or muscle tissue.

36. The method according to claim 34, wherein scarring and contraction that is reduced or treated affects a normal function of a breast, lip, abdominal wall, face, neck, and/or extremities.

37. The method according to claim 34, wherein scarring and contraction is reduced or treated so as to affect the appearance of the patient.

38. The method according to claim 34, wherein the scarring and contraction is at least partly caused by infection, malnutrition, inflammation, systemic diseases, and/or pathological conditions.

39. A method for promoting the filling of a wound cavity and/or tissue defect in a patient, said cavity and/or defect resulting from a procedure and/or trauma following cytoreductive surgery, wherein an effective amount of a pharmaceutical composition comprising an active enamel substance is administered to said wound cavity and/or tissue defect thereby filling the wound cavity and/or tissue defect, and wherein the active enamel substance is enamel matrix, enamel matrix derivatives, or enamel matrix proteins.

40. A method for promoting the re-filling of a wound cavity and/or tissue defect in a patient resulting from a procedure and/or trauma following cytoreductive surgery, wherein an effective amount of a pharmaceutical composition comprising an active enamel substance is administered to said wound cavity and/or tissue defect thereby re-filling the wound cavity and/or tissue defect and, wherein the active enamel substance is enamel matrix, enamel matrix derivatives, or enamel matrix proteins.

41. The method according to any of claim 39 or 40, wherein said administered composition stimulates cellular neogenesis of cells with mesodermal and/or endodermal origin in said wound cavity and/or tissue defect.

42. The method according to any of claim 39 or 40, wherein the cavity or defect is caused by cytoreductive surgery and/or wherein the cavity or defect is at least partly caused by radiation therapy.

43. The method according to claim 42, wherein said cavity or defect is caused by the surgical removal of a tumor selected from the group consisting of mammalian neoplasm, neck and head cancer, abdominal cancer, ovarian cancer, breast cancer and skin cancer.

44. The composition of claim 33, wherein the vehicle is propylene glycol alginate.

* * * * *